United States Patent [19]

Hirota et al.

[11] Patent Number: 4,632,824

[45] Date of Patent: Dec. 30, 1986

[54] COMPOSITIONS APPLIED IN THE MOUTH

[75] Inventors: Kazuo Hirota, Tokyo; Shoji Akahane, Higashikurume; Kentaro Tomioka, Chofu, all of Japan

[73] Assignee: G-C Dental Industrial Corporation, Tokyo, Japan

[21] Appl. No.: 617,817

[22] Filed: Jun. 6, 1984

[30] Foreign Application Priority Data

Jun. 6, 1983 [JP] Japan ................... 58-99522

[51] Int. Cl.⁴ .......... A61K 9/68; A61K 7/16; A61K 7/24; A61K 7/26
[52] U.S. Cl. ................. 424/49; 424/48; 424/55; 424/58; 426/3
[58] Field of Search .......... 424/48, 49, 55, 58

[56] References Cited

U.S. PATENT DOCUMENTS

| | | | |
|---|---|---|---|
| 4,022,880 | 5/1977 | Vinson et al. | 424/55 |
| 4,146,606 | 3/1979 | Yamaga et al. | 424/52 |
| 4,273,758 | 6/1981 | Liau | 424/49 |
| 4,395,398 | 7/1983 | Yamamato | 424/56 |
| 4,524,824 | 6/1985 | Shimokobe et al. | 106/35 |

FOREIGN PATENT DOCUMENTS

| | | | |
|---|---|---|---|
| 0028271 | 5/1981 | European Pat. Off. | 424/49 |
| 0051752 | 5/1982 | European Pat. Off. | 424/49 |
| 54-38180 | 11/1979 | Japan | 424/56 |
| 1130566 | 10/1968 | United Kingdom | 424/49 |
| 2036750 | 7/1980 | United Kingdom | 424/48 |

OTHER PUBLICATIONS

Teraoka, C.A. 90:132633b (1979).
Kaya et al, C.A. 102:119416e (1985).
Payne, C.A. 94:82548n (1981).
Sunstar, C.A. 101:216234f (1984).
Hirota et al, C.A. 102:84271z (1985).
Stralfors, C.A. 66:103797g (1967).
Stralfors, C.A. 70:22920x (1969).
Wrigley, C.A. 77:60323g (1972).
Liao, C.A. 92:153171f (1980).
Sunstar, C.A. 93:173631e (1980).
Weilin, C.A. 95:67823a (1981).
Liau, C.A. 95:86334h (1981).
Liau, C.A. 97:78711e (1982).
Okuda, C.A. 98:221633j (1983).

*Primary Examiner*—Shep K. Rose
*Attorney, Agent, or Firm*—Oblon, Fisher, Spivak, McClelland & Maier

[57] ABSTRACT

A composition applied in the mouth which has a preventive effect on dental carries and contains such tannic acid derivatives as of solubility resistance to water.

4 Claims, No Drawings

COMPOSITIONS APPLIED IN THE MOUTH

FIELD OF THE INVENTION

The present invention relates generally to a composition used in the mouth which has a preventive effect on dental caries, and more particularly to a composition containing tannic acid derivatives being sparingly soluble to water.

BACKGROUND OF THE INVENTION

The wording "compositions applied in the mouth" used in the present disclosure refers to compositions used in the mouth, for instance, for dentifrices in the pastes, powders and gels, mouthwashes and gargles, oral refrigerants in the chewing gum, candy, liquid and pellet forms, caries preventive agents in the paste and liquid forms, tooth make-up agents and the like.

A dentifrice is a substance or preparation used with a toothbrush to aid mechanical cleaning of the accessible surfaces of the teeth. A typical formulation for a dentifrice paste contains abrasives, flavoring mixture, humectants, thickening agents, foaming agents and water. So far, teeth reinforcing agents such as fluorides, enzyme inhibitor such as vitamin K and sodium N-lauroylsarcosine, germicidal agents such as hexylresorcin or nicotinnic acid amide have been used with the dentifrice compositions for the purpose of preventing tooth decay. However, such materials have both merits and demerits, and no utterly satisfactory materials are still found. For instance, it is widely accepted that the fluorides serve to reinforce teeth, but limitations are imposed upon the amount thereof in view of toxicity in vivo. Sodium N-lauroylsarconsine produces a less stimulating action, is of low toxicity and has a strong fermentation preventive action, but is somewhat of a bitter taste and does not have sufficient antibacterial properties. Recent studies have revealed that the traditional "tooth black" used previously in Japan serves to prevent dental caries. The tooth black comprises a powder containing tannic acid as the main component and a solution containing ferrous acetate as the main component. The powder and the liquid are mixed and applied on the teeth. Among these, tannic acid is found to serve to flocculate and astringe tooth protein, whereby tooth is reinforced, and to possess antibacterial and antienzymetic properties useful for the prevention of caries. However, tannic acid easily undergoes coloration, especially blackens, so that it is aesthetically unpreferred. For that reason, extreme restriction is placed upon its use.

SUMMARY OF THE INVENTION

In consequence of intensive studies made of "the compositions applied in the mouth" which contain a substance having a preventive effect as is the case with tannic acid and undergoing no discoloration, it has unexpectedly been found that "the compositions applied in the mouth" containing tannic acid derivatives being sparingly soluble in water are best-suited for that purpose.

DETAILED DESCRIPTION OF THE INVENTION

The wording "substance being sparingly soluble in water" used in the present disclosure refers to tannic acid derivatives which are hardly or slightly soluble in water, inter alia, tannic acid-protein combinations, tannic acid-formaldehyde combinations, acetyl tannic acid and metal tannates.

The protein used for the tannic acid-protein combinations may be of either simple or conjugated type. For example, use may be made of simple protein such as protamin, globulin, albumin, glutelin, prolamin, gelatin and the like as well as conjugated protein such as nucleoprotein, phosphoprotein and the like. Of these protein, particular preference is given to albumin.

No particular limitation is placed upon the metal salts of tannic acid used in the present invention. However, it is preferred to make use of salts of low toxicity (in vivo) such as aluminium, calcium, zinc, magnesium and strontium salts.

Tannic acid derivatives can be added to the compositions applied in the mouth such as dentifrices, mouthwashes and gargles, oral refrigerants, caries preventive agents and tooth make-up agents etc. A mouthwash is a solution for rinsing the teeth and mouth. Generally, a mouthwash serves as an adjunct in cleaning the mouth and as an aid in removing loose debris after brushing. A gargle is liquid to wash mouth and throat especially for medicinal purposes. An oral refrigerant is in such forms as chewing gum, candy, liquid and pellet etc. Chewing gum usually consists of a chicle base, glucose, powdered sugar, starch and flavoring. Other bases may be also used. A caries preventive agent is an agent to have an effect on prevention of caries, for example, fluoride agents (fluoride solutions and gels, fluoride rinses, fluoride containing varnishes). A tooth make-up agent is a kind of cosmetics applied on the teeth. This is similar to nail enamel, namely, it is tooth enamel.

It is to be noted that the compositions according to the present invention may contain other additives in addition to the tannic acid derivatives. For instance, the incorporation of other known substances serving to prevent dental caries poses no problem.

It is also to be noted that the tannic acid derivatives being sparingly soluble in water, as used in the present invention, may be synthesized in various known processes.

The present invention will now be explained in further detail with reference to some examples, to which the invention is not limited.

EXAMPLE 1

Toothpaste was prepared by admixing together the following ingredients.
Dibasic calcium phosphate dihydrate: 43.0% by weight
Glycerin: 12.0
Albumin tannate: 3.5
Sorbitol: 10.0
Sodium carboxymethylcellulose: 0.9
Calcium silicate: 0.3
Sodium lauryl sulfate: 1.8
Distilled water: 27.3
Saccharin: 0.1
Perfume (of the peppermint type): 1.0
Butyl p-oxybenzoate: 0.1

The obtained toothpaste underwent no discoloration after one-day storage.

COMPARATIVE EXAMPLE 1

Toothpaste was prepared by using the composition of Example 1, provided that 3.5% by weight of tannic acid was used in place of albumin tannate. After one-day storage, the resultant toothpaste apparently turned ashen.

COMPARATIVE EXAMPLE 2

Toothpaste was prepared by using the composition of Example 1 free from albumin tannate. After one-day storage, the resultant toothpaste underwent no discoloration.

It was evidently appreciated from the Example 1, Comparative Example 1 and Comparative Example 2 that the toothpaste of Example 1 did not discolore unlike in Comparative Example 1.

EXPERIMENT 1

Plaque estimation was then made with the toothpaste of Example 1 and Comparative Examples 1 and 2.

The marrow was extracted from a fresh tooth pulled out of a cattle, which was in turn sterilized in an ethylene oxide gas sterilizer after ultrasonic washing. A toothbrush (manufactured by GC Dental Industrial Corp. and sold in the trade name of PROSPECK M), to which 1.5 grams of the toothpaste of Example 1 were applied, was reciprocated 200 times for cleaning the surface of that tooth. The thus cleaned tooth was suspended in mitis-salivarius liquid medium in which the overnight-cultured bacteria of *streptococcus mutaos* strains was planted at a concentration of 5%, and was then cultured at 37° C. for 8 hours under gentle stirring with a magnetic stirrer. Thereafter, the test piece was washed with water, dried under reduced pressure in a desiccator to observe the surface of enamel thereof with a scanning electron microscope (SEM).

In another experiment, SEM observation was carried out with a tooth sample which was cleaned in the same manner with a dentifrice-free brush.

In a further experiment, similar SEM observation was undertaken with a tooth sample cleaned with a brush to which albumin tannate-free dentifrice, for instance, those of Comparative Examples 1 and 2, was applied.

In consequence, it was observed that the surface of enamel of the tooth cleaned with the dentifrice-free brush was entirely covered with bacteria and plaque formed. On the contrary, 90% of enamel was covered with bacteria in the case of using the dentifrice of Comparative Example 2. It was also noted that 40% and 35% of enamel were covered with bacteria in the case of using the dentifrice formulations of Comparative Example 1 and Example 1, respectively. From this, it has been appreciated that albumin tannate has an effect upon the inhibition of plaque formation, which indicates that it serves to prevent dental caries.

EXPERIMENT 2

Twelve healthy men (23-29 old) were subdivided into four groups, each comprising three. Group A cleaned the teeth with a brush to which the toothpaste of Example 1, Groups B and C did so with brushes to which the toothpaste of Comparative Examples 1 and 2 was applied, and Group D did so with a dentifricefree brush. Brushing was effected three times a day, say, in the morning, afternoon and evening, and continued for ten days. Brushing was then discontinued for 24 hours. Thereafter, the dirt was rubbed off from the neck of the entire upper jaw teeth located on the cheek with a ready-made applicator, planted in mitis-salivarius liquid medium, and allowed to stand at 37° C. for 48 hours. Subsequently, the pH of the liquid medium was measured with a pH meter. The pH values of Groups A, B, C and D were respectively 6.2, 6.0, 5.6 and 5.2 on the average. It has been appreciated that Group A shows the lowest actvity to caries.

What is claimed is:

1. In a method of treatment of teeth to prevent tooth decay of the surface of teeth on which Streptococcus mutans plaque causing dental caries forms, the improvement over traditional "tooth black", which blackens the teeth, which consists of the step of applying to said teeth a toothpaste, powder, gel, mouthwash, or gargle composition comprising a tannic acid derivative which is sparingly soluble in water, wherein said tannic acid derivative is selected from the group consisting of tannic acid—protein combinations, tannic acid—formaldehyde combinations and acetyl tannic acid in an amount effective to inhibit dental plaque formation.

2. The method of claim 1, wherein said tannic acid—protein combinations are made from a protein selected from the group consisting of protamin, globulin, albumin, glutelin, prolamin, gelatin, nucleoprotein and phosphoprotein.

3. The method of claim 2, wherein said protein is albumin.

4. The method of claim 5, further comprising application in a toothpaste containing dibasic calcium phosphate dihydrate.

* * * * *